US008948532B2

(12) United States Patent
Natanzon et al.

(10) Patent No.: US 8,948,532 B2
(45) Date of Patent: Feb. 3, 2015

(54) SYSTEMS AND METHODS FOR IMAGE HANDLING AND PRESENTATION

(71) Applicant: General Electric Company, Schenectady, NY (US)

(72) Inventors: Alexander Natanzon, Mahwah, NJ (US); Dmitry Pavlov, New Paltz, NJ (US); Alexander Jurovitsky, Mahwah, NJ (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/045,541

(22) Filed: Oct. 3, 2013

(65) Prior Publication Data

US 2014/0029865 A1    Jan. 30, 2014

Related U.S. Application Data

(63) Continuation of application No. 13/718,772, filed on Dec. 18, 2012, now Pat. No. 8,577,163, which is a continuation of application No. 13/407,308, filed on Feb. 28, 2012, now Pat. No. 8,358,863, which is a continuation of application No. 12/275,021, filed on Nov. 20, 2008, now Pat. No. 8,150,175.

(60) Provisional application No. 60/989,375, filed on Nov. 20, 2007.

(51) Int. Cl.
*G06K 9/46* (2006.01)

(52) U.S. Cl.
USPC ............................ 382/239; 382/232; 382/128

(58) Field of Classification Search
USPC ......... 382/239, 232, 128, 305, 131, 132, 294, 382/180; 345/629, 623, 634; 348/473, 699, 348/722; 600/407, 410; 128/922; 378/62; 375/240.16, 240.2
See application file for complete search history.

(56) References Cited

U.S. PATENT DOCUMENTS

| 5,606,648 A | 2/1997 | Walther et al. |
|---|---|---|
| 6,424,996 B1 | 7/2002 | Killcommons et al. |
| 6,671,065 B1 | 12/2003 | Salgado et al. |
| 7,092,965 B2 | 8/2006 | Easwar |
| 7,606,861 B2 | 10/2009 | Killcommons et al. |
| 7,929,793 B2 | 4/2011 | Gering et al. |
| 8,150,175 B2 | 4/2012 | Natanzon et al. |
| 8,326,012 B2 * | 12/2012 | Kreeger et al. ............... 382/132 |

(Continued)

OTHER PUBLICATIONS

United States Patent and Trademark Office, "Notice of Allowance," issued in connection with U.S. Appl. No. 12/275,021, mailed on Nov. 28, 2011, 8 pages.

(Continued)

*Primary Examiner* — Anh Do
(74) *Attorney, Agent, or Firm* — Hanley, Flight and Zimmerman, LLC

(57) ABSTRACT

Certain embodiments provide systems and methods for adaptive compression, transmission, and display of clinical images. Certain embodiments provide a method for adaptive compression of image data for transmission and display at a client workstation. The method includes identifying one or more images for display, the one or more images including a plurality of image slices. The method also includes determining a compression scheme for the one or more images based on at least one of bandwidth, processing power, and diagnostic modality. The method further includes transferring the one or more images for display at the client workstation. The method additionally includes adapting the compression scheme based on resource availability.

20 Claims, 5 Drawing Sheets

(56) References Cited

U.S. PATENT DOCUMENTS

| | | | |
|---|---|---|---|
| 8,358,863 B2 | 1/2013 | Natanzon et al. | |
| 8,547,402 B2 * | 10/2013 | Kreeger et al. | 345/634 |
| 2009/0129643 A1 | 5/2009 | Natanzon et al. | |
| 2012/0163684 A1 | 6/2012 | Natanzon et al. | |

OTHER PUBLICATIONS

United States Patent and Trademark Office, "Non-Final Rejection," issued in connection with U.S. Appl. No. 12/275,021, mailed on Jul. 22, 2011, 5 pages.

United States Patent and Trademark Office, "Notice of Allowance," issued in connection with U.S. Appl. No. 13/407,308, mailed on Oct. 9, 2012, 15 pages.

United States Patent and Trademark Office, "Non-Final Office Action," issued in connection with U.S. Appl. No. 13/718,772, mailed on Mar. 21, 2013, 8 pages.

United States Patent and Trademark Office, "Notice of Allowance," issued in connection with U.S. Appl. No. 13/718,772, mailed on Jul. 2, 2013, 9 pages.

* cited by examiner

SYSTEMS AND METHODS FOR IMAGE HANDLING AND PRESENTATION

RELATED APPLICATIONS

The present application claims the benefit of priority as a continuation of U.S. patent application Ser. No. 13/718,772, filed on Dec. 18, 2012, entitled "Systems and Methods for Image Handling and Presentation", which claims priority as a continuation of U.S. patent application Ser. No. 13/407,308, filed on Feb. 28, 2012, entitled "Systems and Methods for Image Handling and Presentation", which claims priority as a continuation of U.S. patent application Ser. No. 12/275,021, filed on Nov. 20, 2008, entitled "Systems and Methods for Image Handling and Presentation", which claims priority to U.S. Provisional Application No. 60/989,375, filed on Nov. 20, 2007, entitled "Special Methodic for Image Handling and Presentation", each of which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Healthcare environments, such as hospitals or clinics, include information systems, such as hospital information systems ("HIS"), radiology information systems ("RIS"), clinical information systems ("CIS"), and cardiovascular information systems ("CVIS"), and storage systems, such as picture archiving and communication systems ("PACS"), library information systems ("LIS"), and electronic medical records ("EMR"). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

Medical imaging devices now produce diagnostic images in a digital representation. The digital representation typically includes a two dimensional raster of the image equipped with a header including collateral information with respect to the image itself, patient demographics, imaging technology, and other data used for proper presentation and diagnostic interpretation of the image. Often, diagnostic images are grouped in series each series representing images that have some commonality and differ in one or more details. For example, images representing anatomical cross-sections of a human body substantially normal to its vertical axis and differing by their position on that axis from top (head) to bottom (feet) are grouped in so-called axial series. A single medical exam, often referred as a "study" or an "exam" typically includes one or more series of images, such as images exposed before and after injection of contrast material or images with different orientation or differing by any other relevant circumstance(s) of imaging procedure. The digital images are forwarded to specialized archives equipped with proper means for safe storage, search, access, and distribution of the images and collateral information for successful diagnostic interpretation.

BRIEF SUMMARY OF THE INVENTION

Certain embodiments of the present invention provide systems and methods for adaptive compression, transmission, and display of clinical images.

Certain embodiments provide a method for adaptive compression of image data for transmission and display at a client workstation. The method includes identifying one or more images for display, the one or more images including a plurality of image slices. The method also includes determining a compression scheme for the one or more images based on at least one of bandwidth, processing power, and diagnostic modality. The method further includes transferring the one or more images for display at the client workstation. The method additionally includes adapting the compression scheme based on resource availability.

Certain embodiments provide a picture archiving and communications system (PACS). The system includes a PACS server including a plurality of images, the plurality of images including a plurality of image slices. The system also includes a PACS workstation for displaying images. The PACS server and the PACS workstation identify one or more images for display. A compression scheme is determined for the one or more images based on at least one of bandwidth, processing power, and diagnostic modality. One or more images are transferred for display at the client workstation. The compression scheme is adapted based on resource availability.

Certain embodiments provide a computer readable medium having a set of instructions for execution on a computing device. The set of instructions executes a method for adaptive compression of image data for transmission and display at a client workstation. The method includes identifying one or more images for display, the one or more images including a plurality of image slices. The method also includes determining a compression scheme for the one or more images based on at least one of bandwidth, processing power, and diagnostic modality. The method further includes transferring the one or more images for display at the client workstation. The method additionally includes adapting the compression scheme based on resource availability.

Figure 1:
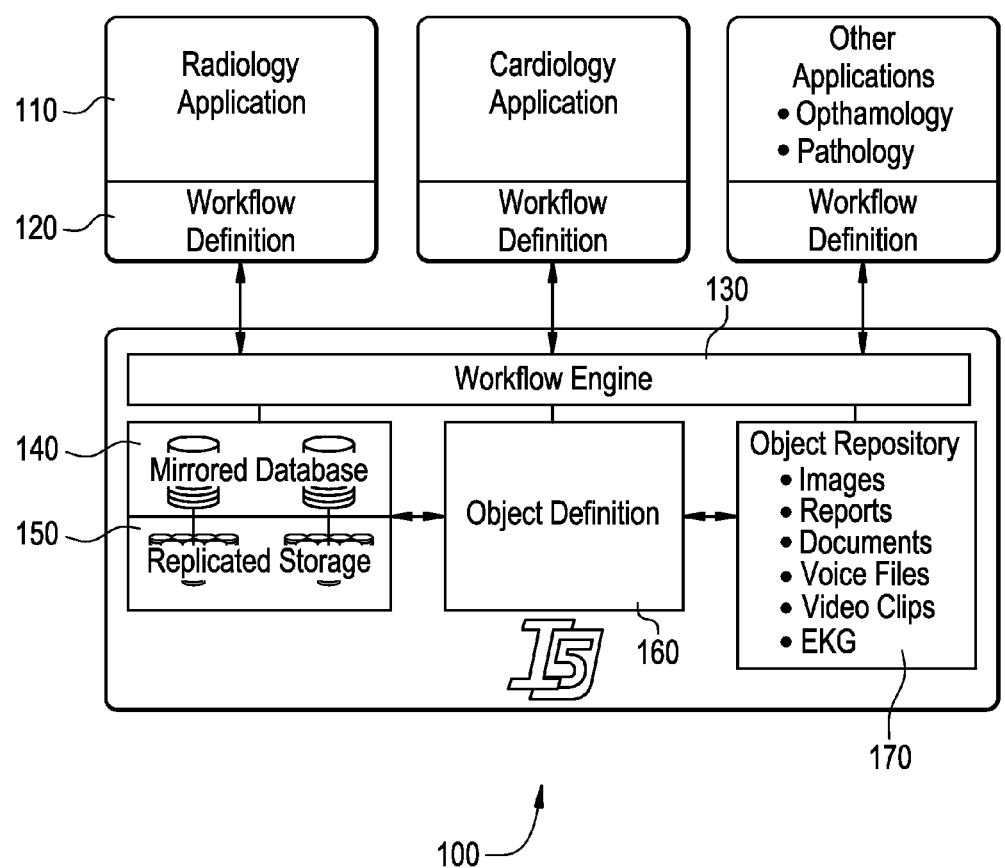
FIG. 1 demonstrates a business and application diagram for PACS information system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments relate to reading and interpretation of diagnostic imaging studies, stored in their digital representation and searched, retrieved, and read using a PACS and/or other clinical system. In certain embodiments, images can be stored on a centralized server while reading is performed from one or more remote workstations connected to the server via electronic information links. Remote viewing creates a certain latency between a request for image(s) for diagnostic reading and availability of the images on a local workstation for navigation and reading. Additionally, a single server often provides images for a plurality of workstations that can be connected through electronic links with different bandwidths. Differing bandwidth can create a problem with respect to balanced splitting of the transmitting capacity of the central server between multiple clients. Further, diagnostic images can be stored in one or more advanced compression formats allowing for transmission of a lossy image representation that is continuously improving until finally reaching a lossless, more exact representation. In addition, a number of images produced per standard medical examination continues to grow, reaching 2,500 to 4,000 images per one typical computed tomography (CT) exam compared to 50 images per one exam a decade ago.

Certain embodiments provide "smart" storage, transfer, usability and presentation of diagnostic images to help alleviate certain problems previously found in digital picture archiving and communication systems (PACS) including but not limited to: (1) a load on an information system, (2) a load on a network data transferring system, (3) heavy requirements to image content storage volume; and (4) latency time for image retrieval, image transmission, and image rendering on a diagnostic workstation's display. Additionally, certain embodiments help facilitate improved ergonomic screen layout, image manipulation, and image presentation for a diagnostic physician to provide more effective visual perception and diagnostic reading.

Prior to archiving, digital images are subjected to different types of compression for minimization of required capacity of storage and bandwidth of information links. One compression standard used in medical imaging and other media content information systems is the JPEG2000 standard, which allows decomposition of an image into multiple compression layers, each layer representing a certain scale and resolution of the image. Transmitting a few of the most coarse layers of the image may be used to represent the general image but may compromise the image quality with respect to finer image details. Although coarse image representation is not sufficient for diagnostic visual perception, it still can be suitable for getting a first impression of anatomical scene, navigating through a stack of images to identify a clinically relevant anatomical area, and/or any other interactive preprocessing of the image or whole medical examination. Subsequent transmission and decompression of additional layers enriches the image with fine details and, upon transmission of all layers, reproduce the image in its exact representation.

In certain embodiments, rather than having only one preferred compression scheme (e.g., jpeg, wavelet, layered, etc.), several compression schemes can be provided in a single system, including uncompressed files. Certain embodiments provide a variety of techniques for handling thin slice data. For example, several thin slices and one thick slice can be combined. Certain embodiments utilize similarity of neighboring images to take advantage of common values to compress images. For example, information common to the slices and information regarding differences between the slices are stored so that the image slices can be compressed using an appropriate mechanism and can be delivered to a workstation on request to enable fine grain reading of diagnostic images. Certain embodiments find applicability for both long term and short term storage depending on a combination of price of storage, price of transfer, load on local and remote networks, price of compression (e.g., time), etc.

Certain embodiments provide systems and methods for transfer, improved storage, and improved presentation and perception of diagnostic images and other viewable media in order to help reduce system cost and complexity as well as physician waiting time and to help improve performance and work quality for a physician (and/or other workstation operator) to implement a workflow associated with reading, reviewing, and/or other utilization of the media.

Certain embodiments provide an information system for a healthcare enterprise including a PACS system for radiology and/or other subspecialty system as demonstrated by the business and application diagram in FIG. 1. The system 100 of FIG. 1 includes a clinical application 110, such as a radiology, cardiology, ophthalmology, pathology, and/or application. The system 100 also includes a workflow definition 120 for each application 110. The workflow definitions 120 communicate with a workflow engine 130. The workflow engine 130 is in communication with a mirrored database 140, object definitions 60, and an object repository 170. The mirrored database 140 is in communication with a replicated storage 150. The object repository 170 includes data such as images, reports, documents, voice files, video clips, EKG information, etc.

Figure 2:
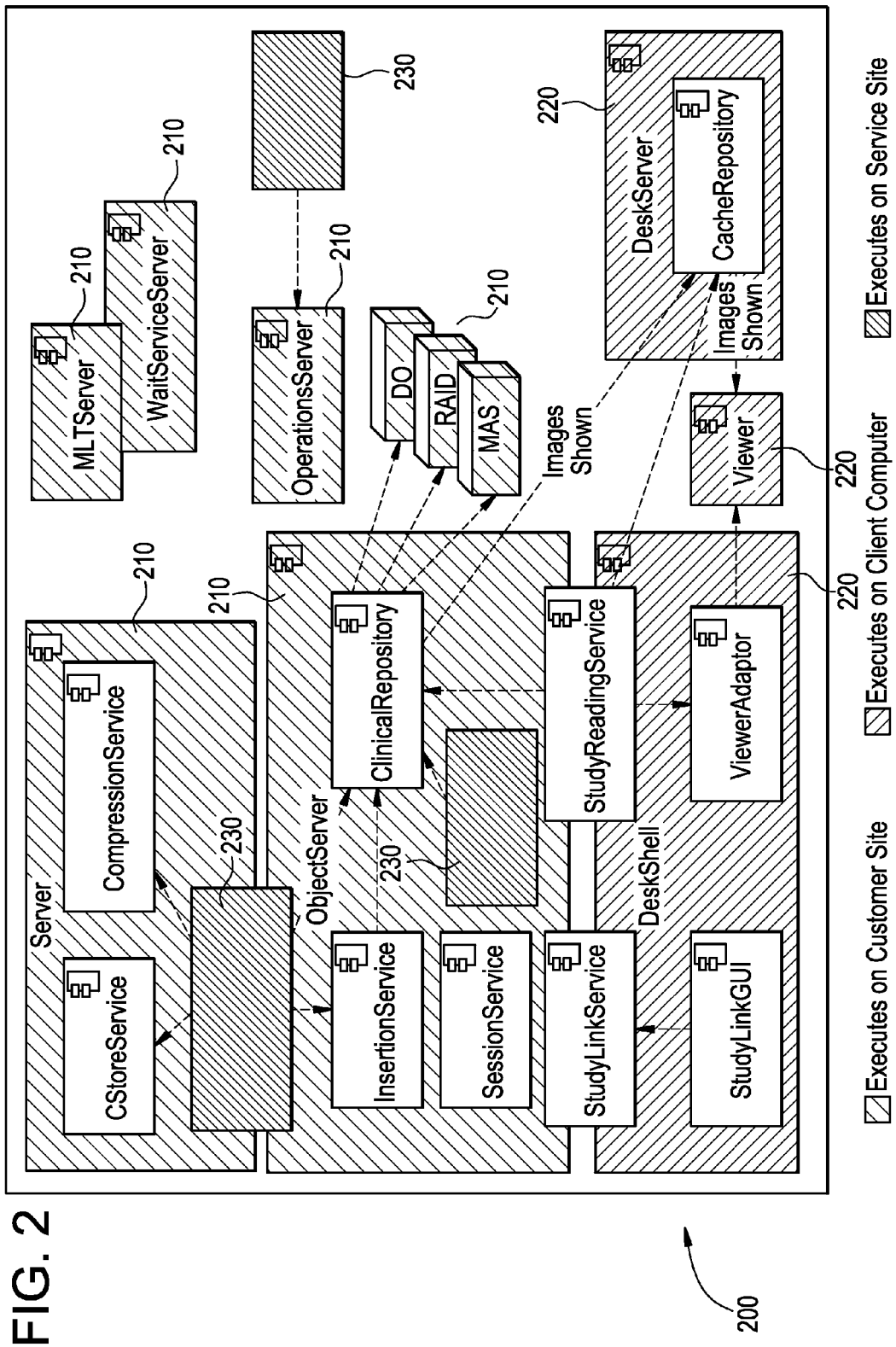
FIG. 2 illustrates an embodiment of an information system delivering application and business content in accordance with an embodiment of the present invention.

An embodiment of an information system that delivers application and business goals is presented in FIG. 2. The specific arrangement and contents of the assemblies constituting this embodiment bears sufficient novelty and constitute part of certain embodiments of the present invention. The information system 200 of FIG. 2 demonstrates services divided among a service site 230, a customer site 210, and a client computer 220. For example, a DICOM Server, HL7 Server, Web Services Server, Operations Server, database and other storage, an Object Server, and a Clinical Repository execute on a customer site 210. A Desk Shell, a Viewer, and a Desk Server execute on a client computer 220. A DICOM Controller, Compiler, and the like execute on a service site 230. Thus, operational and data workflow may be divided, and only a small display workload is placed on the client computer 220, for example.

Certain embodiments provide an architecture and framework for a variety of clinical applications. The framework can include front-end components including but not limited to a Graphical User Interface ("GUI") and can be a thin client and/or thick client system to varying degree, which some or all applications and processing running on a client workstation, on a server, and/or running partially on a client workstation and partially on a server, for example.

Figure 3:
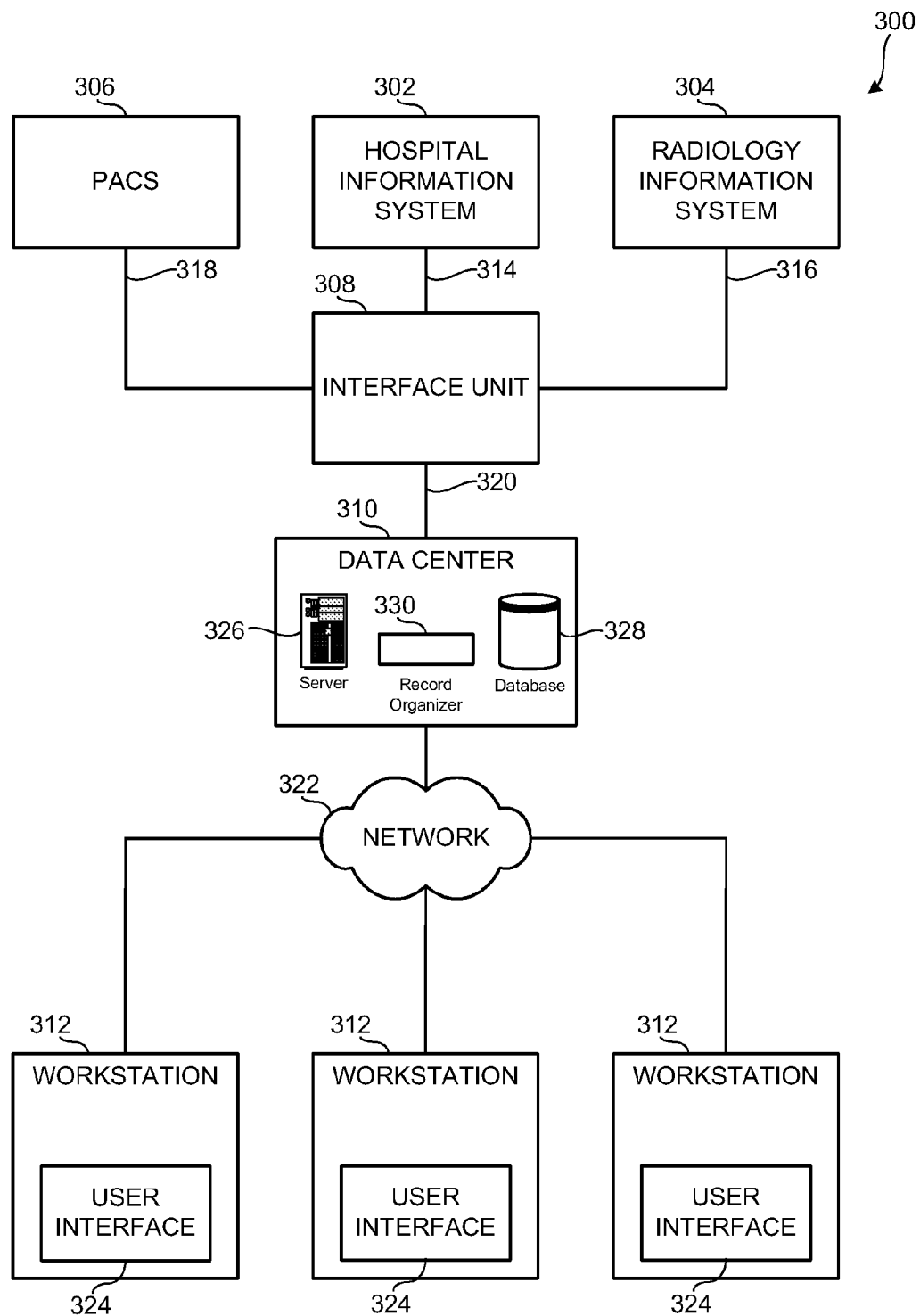
FIG. 3 illustrates a block diagram of an example clinical information system that may be used to implement systems and methods described herein.

FIG. 3 shows a block diagram of an example clinical information system 300 capable of implementing the example methods and systems described herein. The example clinical information system 300 includes a hospital information system ("HIS") 302, a radiology information system ("RIS") 304, a picture archiving and communication system ("PACS") 306, an interface unit 308, a data center 310, and a plurality of workstations 312. In the illustrated example, the HIS 302, the RIS 304, and the PACS 306 are housed in a healthcare facility and locally archived. However, in other implementations, the HIS 302, the RIS 304, and/or the PACS 306 may be housed one or more other suitable locations. In certain implementations, one or more of the PACS 306, RIS 304, HIS 302, etc., can be implemented remotely via a thin client and/or downloadable software solution. Furthermore, one or more components of the clinical information system 300 may be combined and/or implemented together. For example, the RIS 304 and/or the PACS 306 may be integrated with the HIS 302; the PACS 306 may be integrated with the RIS 304; and/or the three example information systems 302, 304, and/or 306 may be integrated together. In other example implementations, the clinical information system 300 includes a subset of the illustrated information systems 302, 304, and/or 306. For example, the clinical information system 300 may include only one or two of the HIS 302, the RIS 304, and/or the PACS 306. Preferably, information (e.g., scheduling, test results, observations, diagnosis, etc.) is entered into the HIS 302, the RIS 304, and/or the PACS 306 by healthcare practitioners (e.g., radiologists, physicians, and/or technicians) before and/or after patient examination.

The HIS 302 stores medical information such as clinical reports, patient information, and/or administrative information received from, for example, personnel at a hospital, clinic, and/or a physician's office. The RIS 304 stores information such as, for example, radiology reports, messages, warnings, alerts, patient scheduling information, patient demographic data, patient tracking information, and/or physician and patient status monitors. Additionally, the RIS 304 enables exam order entry (e.g., ordering an x-ray of a patient) and image and film tracking (e.g., tracking identities of one or more people that have checked out a film). In some examples, information in the RIS 304 is formatted according to the Health Level Seven ("HL-7") clinical communication protocol.

The PACS 306 stores medical images (e.g., x-rays, scans, three-dimensional renderings, etc.) as, for example, digital images in a database or registry. In some examples, the medical images are stored in the PACS 306 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 306 for storage. In some examples, the PACS 306 may also include a display device and/or viewing workstation to enable a healthcare practitioner to communicate with the PACS 306.

The interface unit 308 includes a hospital information system interface connection 314, a radiology information system interface connection 316, a PACS interface connection 318, and a data center interface connection 320. The interface unit 308 facilities communication among the HIS 302, the RIS 304, the PACS 306, and/or the data center 310. The interface connections 314, 316, 318, and 320 may be implemented by, for example, a Wide Area Network ("WAN") such as a private network or the Internet. Accordingly, the interface unit 308 includes one or more communication components such as, for example, an Ethernet device, an asynchronous transfer mode ("ATM") device, an 802.11 device, a DSL modem, a cable modem, a cellular modem, etc. In turn, the data center 310 communicates with the plurality of workstations 312, via a network 322, implemented at a plurality of locations (e.g., a hospital, clinic, doctor's office, other medical office, or terminal, etc.). The network 322 is implemented by, for example, the Internet, an intranet, a private network, a wired or wireless Local Area Network, and/or a wired or wireless Wide Area Network. In some examples, the interface unit 308 also includes a broker (e.g., a Mitra Imaging's PACS Broker) to allow medical information and medical images to be transmitted together and stored together.

In operation, the interface unit 308 receives images, medical reports, administrative information, and/or other clinical information from the information systems 302, 304, 306 via the interface connections 314, 316, 318. If necessary (e.g., when different formats of the received information are incompatible), the interface unit 308 translates or reformats (e.g., into Structured Query Language ("SQL") or standard text) the medical information, such as medical reports, to be properly stored at the data center 310. Preferably, the reformatted medical information may be transmitted using a transmission protocol to enable different medical information to share common identification elements, such as a patient name or social security number. Next, the interface unit 308 transmits the medical information to the data center 310 via the data center interface connection 320. Finally, medical information is stored in the data center 310 in, for example, the DICOM format, which enables medical images and corresponding medical information to be transmitted and stored together.

The medical information is later viewable and easily retrievable at one or more of the workstations 312 (e.g., by their common identification element, such as a patient name or record number). The workstations 312 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 3, the workstations 312 are connected to the network 322 and, thus, can communicate with each other, the data center 310, and/or any other device coupled to the network 322. The workstations 312 are capable of implementing a user interface 324 to enable a healthcare practitioner to interact with the clinical information system 300. For example, in response to a request from a physician, the user interface 324 presents a patient medical history. Additionally, the user interface 324 includes one or more options related to the example methods and apparatus described herein to organize such a medical history using classification and severity parameters.

The example data center 310 of FIG. 3 is an archive to store information such as, for example, images, data, medical reports, and/or, more generally, patient medical records. In addition, the data center 310 may also serve as a central conduit to information located at other sources such as, for example, local archives, hospital information systems/radiology information systems (e.g., the HIS 302 and/or the RIS 304), or medical imaging/storage systems (e.g., the PACS 306 and/or connected imaging modalities). That is, the data center 310 may store links or indicators (e.g., identification numbers, patient names, or record numbers) to information. In the illustrated example, the data center 310 is managed by an application server provider ("ASP") and is located in a centralized location that may be accessed by a plurality of systems and facilities (e.g., hospitals, clinics, doctor's offices, other medical offices, and/or terminals). In some examples, the data center 310 may be spatially distant from the HIS 302, the RIS 304, and/or the PACS 306 (e.g., at General Electric® headquarters).

The example data center 310 of FIG. 3 includes a server 326, a database 328, and a record organizer 330. The server 326 receives, processes, and conveys information to and from the components of the clinical information system 300. The database 328 stores the medical information described herein and provides access thereto. The example record organizer 330 of FIG. 3 manages patient medical histories, for example. The record organizer 330 can also assist in procedure scheduling, for example.

Figure 4:
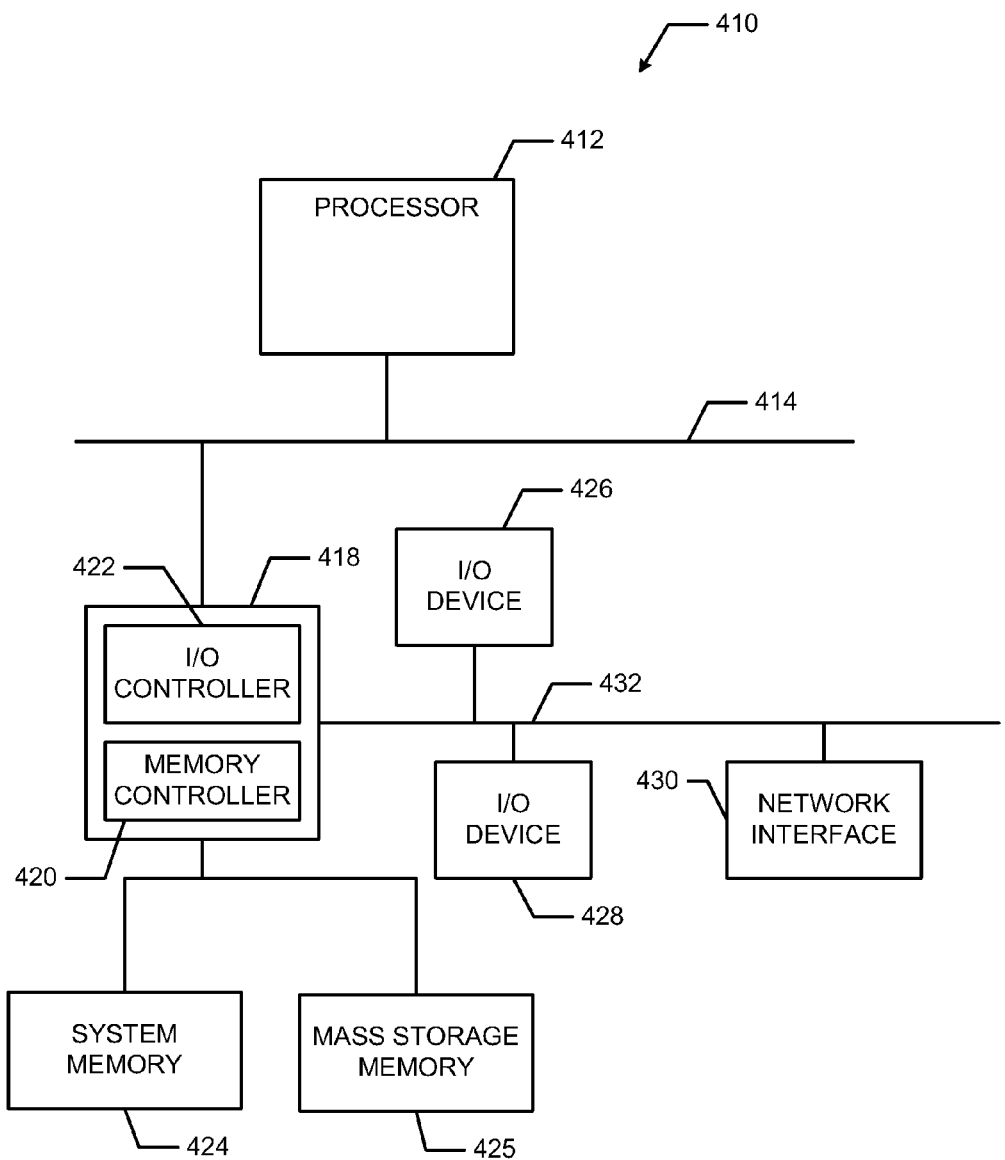
FIG. 4 shows a block diagram of an example processor system that may be used to implement systems and methods described herein.

FIG. 4 is a block diagram of an example processor system 410 that may be used to implement systems and methods described herein. As shown in FIG. 4, the processor system 410 includes a processor 412 that is coupled to an interconnection bus 414. The processor 412 may be any suitable processor, processing unit, or microprocessor, for example. Although not shown in FIG. 4, the system 410 may be a multi-processor system and, thus, may include one or more additional processors that are identical or similar to the processor 412 and that are communicatively coupled to the interconnection bus 414.

The processor 412 of FIG. 4 is coupled to a chipset 418, which includes a memory controller 420 and an input/output ("I/O") controller 422. As is well known, a chipset typically provides I/O and memory management functions as well as a plurality of general purpose and/or special purpose registers, timers, etc. that are accessible or used by one or more processors coupled to the chipset 418. The memory controller 420 performs functions that enable the processor 412 (or processors if there are multiple processors) to access a system memory 424 and a mass storage memory 425.

The system memory 424 may include any desired type of volatile and/or non-volatile memory such as, for example, static random access memory ("SRAM"), dynamic random access memory ("DRAM"), flash memory, read-only memory ("ROM"), etc. The mass storage memory 425 may include any desired type of mass storage device including hard disk drives, optical drives, tape storage devices, etc.

The I/O controller 422 performs functions that enable the processor 412 to communicate with peripheral input/output (I/O) devices 426 and 428 and a network interface 430 via an I/O bus 432. The I/O devices 426 and 428 may be any desired type of I/O device such as, for example, a keyboard, a video display or monitor, a mouse, etc. The network interface 430 may be, for example, an Ethernet device, an asynchronous transfer mode ("ATM") device, an 802.11 device, a DSL modem, a cable modem, a cellular modem, etc. that enables the processor system 410 to communicate with another processor system.

While the memory controller 420 and the I/O controller 422 are depicted in FIG. 4 as separate blocks within the chipset 418, the functions performed by these blocks may be integrated within a single semiconductor circuit or may be implemented using two or more separate integrated circuits.

According to certain embodiments considered as examples in the present application, media files imported from a medical imaging device into a PACS are optionally subjected to a layered incremental compression. Certain media files are grouped in sequences called series, and certain series are grouped into studies, where each study represents a total set of media associated with a single medical exam. Each such study can be optionally attributed to a study type, where each study type is associated with a certain protocol for study interpretation. The protocol can include but is not limited to an order and positions for series display, configuration of a toolbar, annotation and measuring tools, and/or other data required for more efficient presentation of diagnostic images and rendering of a diagnosis. The set of tools and resources is referred to as a "study layout."

For each study registered in the database, an algorithm (e.g., a unique algorithm) exists for creation of a list of respective series and individual images included in the study and selection of a proper layout for study display. Upon getting a request for study display, the server first generates comprehensive lists of media files to be used for reading the study and a related layout for study display. These lists are transferred to a client workstation and copies are kept on the server. According to the generated list of media files and a chosen layout for their presentation on the client workstation, a plan for transferring and optional processing and/or decompression of the media files is built and coordinated between client and server.

According to that plan, a first batch of media transfer includes a minimum amount of compression layers to deliver a coarse enough representation of the image(s) provided such that the coarse representation, while not suitable for diagnostic reading, is sufficient for navigating between the images to review the whole study and then focus on images with high diagnostic value. Upon presentation of the images on the diagnostic or other workstation, tools are offered to an operator for implementation of a diagnostic workflow or other relevant workflow. For example, tools can include but are not limited to: scrolling through the stack of images, adjusting brightness/contrast of the images, making measurements and annotations of the images, rendering some other representation(s) such as three-dimensional ("3D") or oblique slicing, dictation and reporting tools, and/or other relevant tools.

A variety of image display and manipulation tools and other functionality can be provided by the PACS framework described above. The following description details several examples for purposes of illustration only.

A First Embodiment

According to a first embodiment, an interactive control is provided for scrolling through images representing successively adjacent and substantially parallel geometrical cross-sections of a human body anatomy (or its functional mapped representation) that are combined in same image series. According to government and professional regulations, a diagnostic physician is responsible for visual perception of all clinical evidence collected under each diagnostic exam. Visual perception is usually carried out in the process of routine scrolling of the whole image stack consolidated in the same image series. Thus, presentation software facilitates display of each successive image for a reasonable period of time upon such interactive scrolling. In traditional systems, this functionality is implemented using a pointing device (e.g., a mouse, trackball, or other type of device) whereby display of the next image is triggered upon identification of screen cursor displacement over certain pre-defined number of screen pixels. This simplistic implementation suffers from a dependency on the scrolling time of the overall image stack as a function of image slice thickness.

For purposes of illustration and example only, consider a whole body scan of a 180 cm (~6 feet) height patient. Suppose, for example purposes only, that each image of this scan bears information with respect to an anatomical slab of 5 mm thickness (which is typical for Magnetic Resonance diagnostic exams)—thus producing total of 360 images for the whole body scan. Also suppose that the example system is rigidly configured in such a way that display of the next image in the image stack is triggered by displacement of the screen pointer by 3 screen pixels. Then, to scroll through the entire image stack, the pointing device cursor or indicator is moved across 1080 screen pixels or approximately the vertical size of most of consumer monitors and about the half-height of a typical medical imaging monitor. Alternatively, for example, consider a whole body scan upon computed tomography (CT) medical examination with a typical slice thickness of 0.67 111 m—thus providing 2,700 images. If displayed on the same system as described in previous example, scrolling of this image stack would involve displacement of the pointing device by about eight thousand pixels, which is about eight times the size of consumer monitors or about three times of the size of highest resolution medical monitors.

In the first embodiment, a relation between a pointing device displacement used to trigger display of a next image in a stack is set adaptively to a slice thickness in such a way that a total displacement of a pointing device screen cursor or indicator by a predefined number of screen pixels causes scrolling of a plurality of images that substantially sweep a predefined length of anatomical volume, independent of a separation between geometrical locations of adjacent images.

That is, depending upon image characteristics (e.g., anatomy, modality, zoom, etc.), a user may run out of room or display area on the screen when moving a mouse to scroll through a series of images. Certain embodiments mitigate an effect of slice thickness. The interface can be configured such that moving a display cursor by two pixels should cause a displacement of two millimeters in the imaged anatomy. Alternatively, the interface can be configured so that moving a display cursor from top to bottom in a viewport scrolls the image stack from top image to bottom image. In certain embodiments, a mouse or cursor movement mode can be managed through regular movement, through an additional button press, etc.

A Second Embodiment

In the first embodiment, described above, image stacks are scrolled more ergonomically regardless of substantially differing spatial separation between adjacent images. In a second embodiment, substantially identical image stacks can be scrolled through on a plurality of workstations that differ in monitor resolution. In such resolution-varying systems, a displacement of a physical pointing device, such as a mouse, trackball or other device, by the same physical distance results in substantially different displacements of the screen cursor as measured in screen pixels. Varying cursor displacements in turn results in scrolling through a substantially different plurality of the images on each workstation. According to the second embodiment, a control system can be adaptively configured such that a physical displacement of a pointing device by a predefined physical measure results in scrolling through substantially the same number of images independent of a screen resolution and/or other properties and parameters of a physical device and/or a workstation on which the images are being displayed.

That is, mouse or displayed cursor travel is connected with displayed pixels. If a user moves, for example, from an office computer to a home computer with different pixel and/or display size, a display measure is connected to a slice stack measure to facilitate image stack navigation and display. For example, a percentage of a human body and/or a percentage of an image slice stack can be mapped to a percentage of a display, a dimension of the display (e.g., centimeters, millimeters, etc.), a fraction of a placeholder, etc.

A Third Embodiment

A third embodiment is a combination of the first and second embodiments. According to the third embodiment, a scrolling control subsystem can be configured such that a physical displacement of a pointing device by substantially the same physical measure results in scrolling through a plurality of images that substantially sweep a predefined length of an anatomical volume independent of a separation between geometrical locations of adjacent images and also independent of properties and parameters of a physical device and/or a workstation upon which the images are being viewed.

A Fourth Embodiment

According to a fourth embodiment, continuous scrolling of the images can be triggered by an action other than use of a pointing device. For example, triggering can be implemented by pressing and holding a key, button, or pedal and/or through another physical trigger. According to the fourth embodiment, scrolling speed is adjusted such that within a predetermined time interval an image stack is scrolled through a plurality of images that substantially sweep a predefined length of an anatomical volume independent of a separation between geometrical locations of adjacent images.

Thus, for example, a user can trigger scrolling, and images are scrolled automatically until the user releases the trigger. Scrolling speed is dependent not only on slice numbers but also on a progressing of the slices through their position in the human body (e.g., one inch per second or the whole stack of images is scrolled through in 10 seconds to provide an overview).

A Fifth Embodiment

According to a fifth embodiment, diagnostic images imported by a PACS do not undergo immediate compression if a bandwidth of one or more information links used for delivery of the images to the workstation(s) is wide enough to facilitate prompt downloading of images to the local workstations. The "wide enough" criteria can be established in a plurality of ways including but not limited to: (1) determined by a direct assessment of the actual bandwidth of the data links, (2) set manually upon configuration of the system, (c) a combination of above, etc. According to this embodiment, diagnostic images stored in the system can be further optionally subjected to "aging" compression to reduce a volume of long term storage to either lossless or lossy quality. An exact compression ratio formula can be based on a combination of factors that can be assessed individually for each image or collectively for a plurality of images. Factors include but are not limited to a combination of: diagnostic modality, nature of exam, time elapsed from exam itself and/or from last access to the image(s), institution and/or governmental regulations, etc. The "aging compression" can be optionally scheduled for "low CPU usage hours" and triggered by a combination of factors, the exact formula based on but not limited to combination of: age of the images, time elapsed since last access to images, diagnostic modality and/or nature of the exam, regulations and preferences of institutions, societies and individuals, and/or other factors.

Compression algorithms often attempt to squeeze the volume of the image data as close as possible to a minimum. With multi-slice CT, for example, image data occupies gigabytes because the entry level and images reside on a computer but must be uncompressed, a process which takes time, especially for images processed and compressed by a third party system. Images can be prioritized such that an active image receives priority for loading and the next image behind the active image receives priority as well. If a certain compression method fails to provide sufficient throughput and/or response time, network shortcomings may be addressed instead. For example, a three dimensional viewer may need all volume data decompressed rather than using partial data. Therefore, in certain cases, images may not be compressed at all.

Thus, certain embodiments provide adaptive compression to determine whether to compress or provide image data uncompressed or to provide a combination of compressed and uncompressed image data. In certain embodiments, a PACS server may store two copies, one compressed and one non-compressed, and choose which one to transfer. May choose, for example, if within hospital use non-compressed.

As an example, if a physician is working from home, compression of image data may be appropriate, but the user may not need adaptive compression with prioritization. In certain embodiments, the system can adjust the compression method dynamically as data is being transferred. For example, a transfer may begin with compressed data and then determine that all the images should be transferred for viewing rather a sequence of one by one. However, available processing power may be lower than available bandwidth on the transmission line, so the bottleneck is due to compression. As a result, the remainder of transferred images can be transferred using a decompressed representation. Transmission status can be reviewed again and transmission/compression format can be changed again. Thus, aging compression involves evaluating image data transmission and compression and adjusting compression and/or image resolution based on transmission status, for example.

A Sixth Embodiment

According to a sixth embodiment, similar to the fifth embodiment described above, images are delivered to a viewing workstation either in a compressed or in an original (non-compressed) format. A decision regarding the delivery format is made by a formula based on a combination of certain factors including but not limited to: a bandwidth of an information link between server and workstation, a type of information link (e.g., local area network (LAN), wide area network (WAN), Internet, virtual private network (VPN), other), processing power of the workstation, institution policy, individual preferences, etc. One or more of the selected factors can be (a) set manually upon configuration of the system and/or setting policy and/or preferences; (b) assessed automatically upon system functioning; (c) by combination of the above; and/or (d) by other suitable method. Selective delivery can be facilitated by keeping multiple copies of the same data in all involved formats or by "on-demand" preparation of a particular format from one or more storage format(s) by a processing engine.

A Seventh Embodiment

According to a seventh embodiment, images and data used for rendering a first screen on a display workstation and initiating a corresponding interactive or automated workflow are delivered in a special "start up" format. The format is one effective for reducing latency time in awaiting the first visual screen and/or other resources for initiation of the workstation's workflow. The start-up format is defined by a formula based on a combination of certain factors including but not limited to: bandwidth of an information link between server and workstation, a type of link (e.g., LAN, WAN, Internet, VPN, etc.), processing power of the workstation, institution policy, individual preferences, etc. One or more of the selected factor(s) can be (a) set manually upon configuration of the system and/or setting policy and/or preferences; (b) assessed automatically upon system functioning; (c) by a combination of the above; and/or (d) by other suitable method.

The "start-up" data format can be predetermined and securely stored on the server, or created on-demand by conversion from a storage format by a processing engine. Subsequent data delivered to the workstation after initiation start-up screen and workflow can be delivered by other loading format(s) and/or other loading plan(s) including but not limited to those disclosed in other embodiments.

The special start up or initial format can be implemented in a variety of ways. For example, the special format can be an overview screenshot of certain images but not a single individual image. This first content for the screen can be prepared in advance. An image study can be reviewed to create a metadata file describing the whole study but not building the study. Building the study can be performed by retrieving images with the same study number from an image database, for example, and delivered to a client workstation in digested form while the pre-form first content (e.g., a static first view) is being displayed to a reviewing physician at the client workstation. For example, a pre-generated first view typical for that workstation, such as a static overview image, can be provided to allow the physician to spend a few seconds looking rather than being idle and waiting for image delivery.

An Eighth Embodiment

According to an eighth embodiment, an information system imports a series of images that represent substantially parallel cross-sections of a patient anatomy and sweep some anatomical volume with high density of substantially adjacent image. Thus, the series of images provides high spatial resolution at least in a direction normal to the planes of cross-sections. According to this embodiment, the image series can be subjected to "aging consolidation" by grouping an initial series of images into a plurality of spatially confined and successively adjacent groups of images and consolidating a plurality of consecutive images belonging to a same spatially confined group into one image or another plurality of images with reduced spatial resolution while substantially representing an anatomical slab covered by a respective group of initially non-consolidated of images.

Image slice consolidation can be achieved by a variety of methods including but not limited to: combining respective pixels of neighboring images into one pixel; combining a plurality of neighboring pixels of the same image into one pixel; and/or combining respective groups of neighboring pixels on neighboring slices into one pixel, for example.

As discussed above, combining respective pixels of neighboring images into one pixel can be achieved by a variety of methods including but not limited to: mean value, median value, maximum value, minimum value, etc. Combining a group of neighboring pixels of the same image into one pixel can be achieved by a variety of methods including but not limited to: mean value, median value, maximum value, minimum value, etc. Combining respective groups of neighboring pixels on neighboring slices into one pixel can be achieved by a variety of methods including but not limited to: mean value, median value, maximum value, minimum value, etc.

The method used and consolidation formula are based on the combination of factors including but not limited to: diagnostic modality, initial spatial resolution, nature of exam, time elapsed from exam and/or from last access to the data, institution and/or governmental regulations, etc. Consolidation can be scheduled for "low CPU usage hours" and triggered by a scheduling formula based on a combination of factors including but not limited to: age of the images; time elapsed since last access to images, diagnostic modality and/or nature of the exam, regulations and preferences of institutions, societies and individuals, etc.

CT scanners can produce slices with a thickness of less than 1 mm with high resolution. Rendering three dimensional images involves slices with high resolution. Sometimes high resolution is used when looking for tiny details (e.g., vessels, plaque on vessel walls, etc.) in images. To store these high resolution slices is expensive as is transferring them because a wide bandwidth network is used. Therefore, dedicated workstations are often configured to use high resolution data, which they then send to a PACS workstation as consolidated data (e.g., averaging image data across four slices of 0.7 mm into one slice of 3 mm) so that the PACS workstation displays images of inferior quality to dedicated workstations. However, the PACS can store patient history information and includes diagnostic tools, etc.

Rather than forcing a physician to physically move to a dedicated viewing workstation for better presentation but no additional patient information, which often involves moving from a dark room to a light room and back to a dark room (thus interfering with a physician's vision), certain embodiments provide launching of all such content from a PACS workstation. If a server or other system sends lower resolution data to a PACS workstation and then needs to send high resolution data, two sets of data (e.g., one low resolution and one high resolution) can be sent.

A Ninth Embodiment

According to a ninth embodiment, the eighth embodiment is modified such that in addition to producing a set of consolidated lower resolution images, a difference between initial data and consolidated data is calculated and stored in the system in a form targeted for substantial preserving of high resolution data for its optional usage when diagnostic quality of low resolution consolidated images is not sufficient. Calculating and storing the difference can help improve storage performance and/or reduce storage cost, for example. Storage of the difference between high resolution and low resolution data can include but is not limited to following: the difference is converted to compressed lossless or lossy format and stored together with consolidated data; the difference is converted to another reduced resolution format stored together with consolidated data; the difference is converted to an appropriate format including but not limited to compressed and/or reduced resolution and/or original format, but stored in some storage other than the storage used for consolidated data with lower price per megabyte or for any other practical reason, for example.

Thus, a physician or other user of the system can access aged images with reduced spatial resolution, while having an ability to access the full resolution images in a substantially representative appearance. The substantially representative appearance of the full resolution data can be reconstructed in advance or on-demand by adding to each consolidated image the difference between original image and consolidated one. The difference can be pre-calculated as part of the aging consolidation, for example.

As an example, a reference frame can be stored along with a difference between each reference frame and surrounding intermediate frames. As another example, rather than using every tenth frame as representative image data, an average of each consecutive ten frames is determined to generate a consolidated representation of the anatomical value. Thus, a thick image slice can be created that has image data values as if the slice was generated with an old modality at thickness of, for example, 3 mm rather than 0.7 mm The thicker slice may be good for comparison but not for sophisticated volume rendered or analysis applications, for example.

For the remainder of the image data, there are many economical ways to store that difference data. For example, a lossy compression can be used to make compromises on low level details but maintain high level difference information between images. Difference data can be maintained on a remote storage with high latency access but low cost, for example. The difference data can have its own life cycle and plan. For example, image difference data may be kept whole on an image archive and, after a year, be subject to lossy compression for further storage. After another year, the compressed data is subject to another lossy compression, and, after five years, the archived difference data is deleted, for example.

Figure 5:
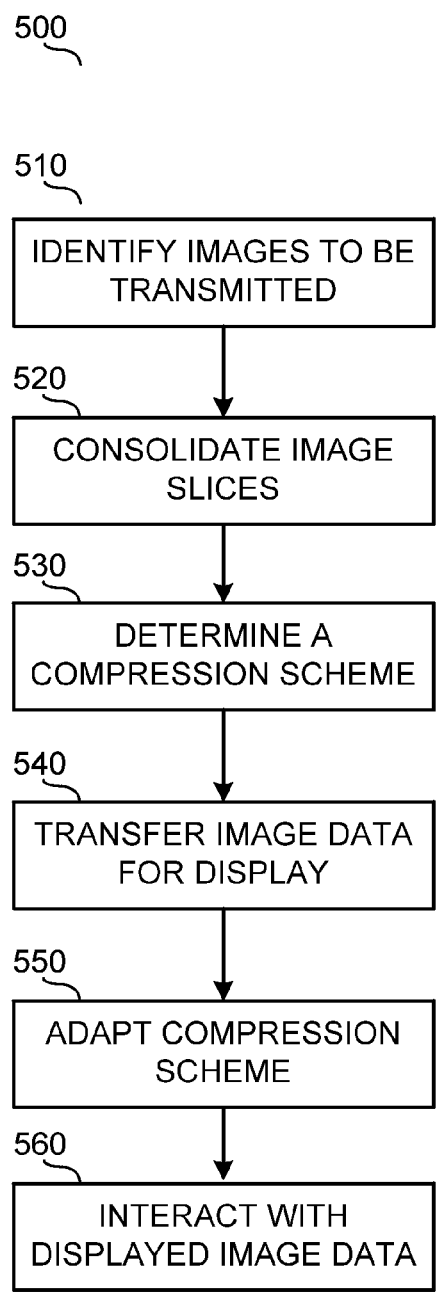
FIG. 5 illustrates a flow diagram for a method for adaptive compression according to certain embodiments of the present invention.

FIG. 5 illustrates a flow diagram for a method 500 for adaptive compression according to certain embodiments of the present invention. At 510, one or more images to be transmitted are identified. For example, an image study including a plurality of image slices from a patient exam is requested for viewing at a PACS workstation.

At 520, image slices are combined or consolidated according to one or more combination schemes. For example, several thin slices and one thick slice can be combined. Similarity of neighboring images can be used to identify common image information and difference information distinguishing slices from the common values. As another example, an image series can be grouped into a plurality of spatially confined and successively adjacent groups of images, where consecutive images belonging to the same spatially confined group are consolidated into one image. Respective pixels of neighboring images can be combined into one pixel, for example, such as by mean value, median value, maximum value, minimum value, etc. As a further example, a difference between initial data and consolidated data is determined and stored. Difference data can be used with consolidated data when high resolution images are displayed, and consolidated data can be used without difference data for coarser images, for example. Consolidated data and difference data can be stored, compressed, and/or transmitted differently, for example.

At 530, an applicable compression scheme is determined for the transmitted image data. For example, several compression schemes can be provided, including jpeg, wavelet, layered, uncompressed, etc. Common values and difference information for a series of image slices can be compressed separately according to the same or different compression scheme, for example. Imported media files can be subjected to a layered incremental compression, for example. Adaptive compression determines whether to provide compress image data, uncompressed image data, or a combination of compressed and uncompressed image data. In an embodiment, a PACS server can store both compressed and uncompressed copies of image data and select which copy to transfer. In an embodiment, data transmission bandwidth is analyzed to determine whether compression is warranted for data or if the bandwidth is wide enough for uncompressed data transmission. In certain embodiments, a compression ratio formula can be based on a combination of factors related to individual images and/or groups of images such as bandwidth, processing power, diagnostic modality, exam type, time elapsed, regulations, etc. Compression selection can be made automatically based on certain parameters, including but not limited to those described above, can be set manually, or can be set by a combination of automated and manual selection.

At 540, image data is transferred to a client workstation for display. As an example, a first batch of image data transfer includes a minimum amount of compression layers to deliver a coarse representation of the image(s) sufficient for a user to navigate between images to review the study and further request and focus on images of high diagnostic value. For example, a start-up or initial image may be provided for initial user review while full image slices are being loaded in the background for subsequent display.

At 550, a compression and/or transfer scheme is adapted based on resource availability. For example, transfer link bandwidth, link type, processing power, viewing application requirements, government regulations, user preference, etc., can be used to adapt a compression and/or consolidation scheme for image data.

At 560, a user can interact with the displayed image data. For example, pointing device displacement can be set adaptively to image slice thickness such that a total displacement of a pointing device by a predefined number of screen pixels causes scrolling of a plurality of image slices that sweep a predefined anatomical volume regardless of slice thickness. As another example, a physical displacement of a pointing device by a predefined physical measure results in scrolling through substantially the same name number of image slices independent of screen resolution, device properties, and/or workstation parameters (e.g., a percentage of a human body and/or a percentage of a stack of image slices can be mapped to a percentage or dimension of a workstation display for viewing). As a further example, scrolling of image slices can be triggered, and images are scrolling based on an adjustable scrolling speed such that a certain anatomical volume and/or stack of images is displayed within a certain time period.

One or more of the steps of the method 500 may be implemented alone or in combination in hardware, firmware, and/or as a set of instructions in software, for example. Certain examples may be provided as a set of instructions residing on a computer-readable medium, such as a memory, hard disk, DVD, or CD, for execution on a general purpose computer or other processing device.

Certain examples may omit one or more of these steps and/or perform the steps in a different order than the order listed. For example, some steps may not be performed in certain examples. As a further example, certain steps may be performed in a different temporal order, including simultaneously, than listed above.

Thus, certain embodiments provide different methods for packaging image data for delivery and display. Currently, most PACS utilize one preferred compression scheme (e.g., jpeg, wavelet, or layered). Certain embodiments provide a plurality of compression methods in one system, including uncompressed files, for selection based on network and system constraints. Additionally, different methods for handling thin slice data are provided. For example, several thin slices and one thick slice can be combined for transmission and display. As another example, compression utilizing similarity of neighboring images is used to take advantage of common values to compress image data. Common or reference information is stored as well as information regarding differences between the slices so that these can be compressed using the appropriate mechanism and can be delivered to workstation(s) on request to enable fine reading. Certain embodiments provide methods and systems useful for both long term and short term storage depending on a combination of price of storage, price of transfer, load on local and remote networks, and price of compression (time), for example. Certain embodiments provide a technical effect of adaptive compression and packaging of image data for transmission and display, for example.

It should be understood by any experienced in the art that the inventive elements, inventive paradigms and inventive methods are represented by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method comprising:
   identifying, using a processor, a plurality of image slices in a study stored at a source for transmission and display via a client;
   generating a list of media files including the plurality of image slices and associated layout information for display of the study via the client;
   building a plan, according to the generated list of media files and associated layout information, to transfer the media files to the client workstation for display according to a compression and decompression scheme, the plan coordinated between the source and the client and including a coarse representation of the study to facilitate navigation between the image slices followed by the media files representing the plurality of image slices;
   facilitating transfer, using the processor, of the coarse representation and the list of media files to the client according to the plan; and
   adapting, using the processor, the plan based on resource availability.

2. The method of claim 1, wherein the plan includes instructions to process the list of media files at the client.

3. The method of claim 1, further comprising determining, using the processor, a compression scheme for the combined image slice data based on at least one of bandwidth, processing power, and diagnostic modality to generate compressed, combined image slice data represented by the list of media files.

4. The method of claim 1, wherein the coarse representation is formed using a minimum number of compression layers to deliver the coarse representation rather than a diagnostic quality image.

5. The method of claim 1, further comprising, upon presentation of the image slices at the client, providing tools via the client to implement a diagnostic workflow with respect to the image slices at the client.

6. The method of claim 5, wherein the tools facilitate one or more of: a) scrolling through the image slices, b) adjusting at least one of brightness and contrast of the image slices; c) making measurements and annotations of the images, d) rendering an alternative representation of the image slices; and e) reporting with respect to the image slices.

7. The method of claim 1, wherein the compression and decompression scheme includes one or more of jpeg compression, wavelet compression, layered compression, layered incremental compression, and uncompressed.

8. The method of claim 1, further comprising combining, using the processor, the image slices according to one or more image slice combination schemes to generate combined image slice data represented by the list of media files.

9. The method of claim 8, wherein the one or more combination schemes includes combining a plurality of neighboring thin image slices with a thicker image slice and identifying common image information as consolidated data for the combined image slice, the combination scheme forming difference data to distinguish slices from the common image information.

10. The method of claim 9, wherein the consolidated data and difference data are compressed according to different compression and decompression schemes.

11. A non-transitory computer readable storage medium having a set of instructions for execution on a computing device, the set of instructions executing a method comprising:
   identifying a plurality of image slices in a study stored at a source for transmission and display via a client;
   generating a list of media files including the plurality of image slices and associated layout information for display of the study via the client;
   building a plan, according to the generated list of media files and associated layout information, to transfer the media files to the client workstation for display according to a compression and decompression scheme, the plan coordinated between the source and the client and including a coarse representation of the study to facilitate navigation between the image slices followed by the media files representing the plurality of image slices;
   facilitating transfer of the coarse representation and the list of media files to the client according to the plan; and
   adapting the plan based on resource availability.

12. The computer readable storage medium of claim 11, wherein the plan includes instructions to process the list of media files at the client.

13. The computer readable storage medium of claim 11, wherein the method further comprises determining, using the processor, a compression scheme for the combined image slice data based on at least one of bandwidth, processing power, and diagnostic modality to generate compressed, combined image slice data represented by the list of media files.

14. The computer readable storage medium of claim 11, wherein the coarse representation is formed using a minimum number of compression layers to deliver the coarse representation rather than a diagnostic quality image.

15. The computer readable storage medium of claim 11, wherein the method further comprises, upon presentation of the image slices at the client, providing tools via the client to implement a diagnostic workflow with respect to the image slices at the client.

16. The computer readable storage medium of claim 15, wherein the tools facilitate one or more of: a) scrolling through the image slices, b) adjusting at least one of brightness and contrast of the image slices; c) making measurements and annotations of the images, d) rendering an alternative representation of the image slices; and e) reporting with respect to the image slices.

17. The computer readable storage medium of claim 11, wherein the compression and decompression scheme includes one or more of jpeg compression, wavelet compression, layered compression, layered incremental compression, and uncompressed.

18. The computer readable storage medium of claim 11, wherein the method further comprises combining, using the processor, the image slices according to one or more image slice combination schemes to generate combined image slice data represented by the list of media files.

19. The computer readable storage medium of claim 18, wherein the one or more combination schemes includes combining a plurality of neighboring thin image slices with a thicker image slice and identifying common image information as consolidated data for the combined image slice, the combination scheme forming difference data to distinguish slices from the common image information.

20. The computer readable storage medium of claim 19, wherein the consolidated data and difference data are compressed according to different compression and decompression schemes.

* * * * *